US00PP28528P2

(12) United States Plant Patent
Horvath

(10) Patent No.: US PP28,528 P2
(45) Date of Patent: Oct. 10, 2017

(54) ***SEDUM* PLANT NAMED 'PILLOW TALK'**

(50) Latin Name: ***Sedum* hybrid**
Varietal Denomination: Pillow Talk

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 40 days.

(21) Appl. No.: 14/757,353

(22) Filed: Dec. 22, 2015

(51) Int. Cl.
*A01H 5/02* (2006.01)

(52) U.S. Cl.
USPC ..... Plt./479

(58) Field of Classification Search
USPC ..... Plt./479
See application file for complete search history.

(56) References Cited

PUBLICATIONS

American Nurseryman Dec. 10, 2015 New Plants 2016: Intrinsic Perennial Gardens Inc., retrieved on Mar. 30, 2017, retrieved from the Internet at <http://www.amerinursery.com/plants/new-plants-2016-intrinsic-perennial-gardens-inc/> 9 pp.*

* cited by examiner

*Primary Examiner* — June Hwu

(57) ABSTRACT

A new, distinct *Sedum* plant as illustrated and described, characterized by large green foliage, red-purple color flowers, and taller height.

1 Drawing Sheet

Latin name: *Sedum* hybrid.
Cultivar name: 'Pillow Talk'.

BACKGROUND OF THE INVENTION

The present invention relates to a new and distinct hybrid of *Sedum* plant named 'Pillow Talk' characterized by larger green foliage, red-purple color flowers, taller height compared to the seed parent. The new *Sedum* was raised as a seedling from open pollinated seed sown as an unnamed *Sedum ussuriense*, not patented, in Hebron, Ill. in 2013. The selection of the new plant was due to its' larger green foliage, deep red-purple color flowers, taller height, compared to the seed parent. Initial asexual reproduction has taken place at a nursery in Hebron, Ill. since 2014 by means of division, and vegetative stem cuttings. The new *Sedum* has shown to be stable and identical in reproduction to the originally discovered plant after rooting over 700 plants from 2014 to 2015. No plants of the new *Sedum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Sedum* plant named 'Pillow Talk' characterized by larger green foliage, red-purple color flowers, taller height, compared to the seed parent have been observed to be unique and stable.

Plants of the new *Sedum* can be compared to plants of *Sedum spectabile* 'Brilliant' not patented. 1. The new *Sedum* plant has a mature size measuring 45-50 cm high and up to 90 cm wide while *Sedum spectabile* measures 45-55 cm high and 55-65 cm wide. 2. The new *Sedum* has red-purple flowers while *Sedum spectabile* is entirely pink.

Plants of the new *Sedum* can also be compared to the seed parent plant, an unnamed, *Sedum ussuriense*, not patented. 1. The new *Sedum* has a mature size of 45-50 cm high and 90 cm wide while the seed parent has a mature size of 30 cm high and 30 cm wide. 2. The new *Sedum* has larger foliage measuring on average up to 11 cm long by 7 cm wide while the seed parent has foliage measuring 40 mm long by 35 mm wide. 3. The new *Sedum* has a stem diameter of 13 mm while the seed parent has stem diameter of 3 mm. 4. The new *Sedum* has red-purple flowers, compared to the mostly red flowers of the seed parent.

DESCRIPTION OF PHOTOGRAPHS

Figure 1:
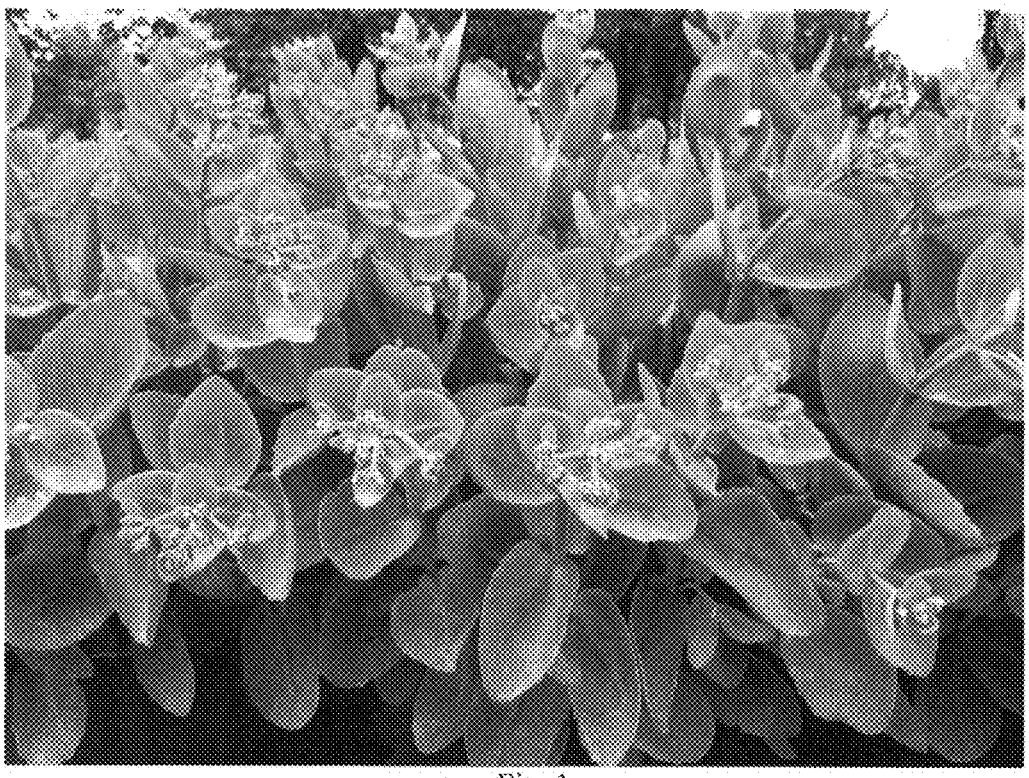
Figure 2:
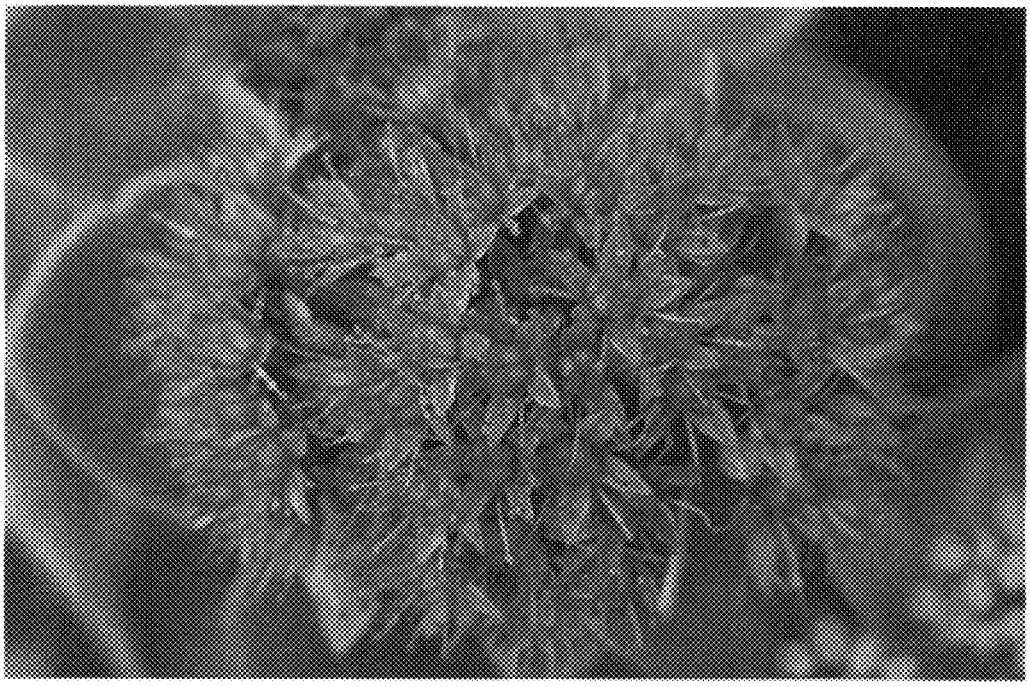

Plants pictured in the drawing were grown for two years.
FIG. 1. Close up of the foliage.
FIG. 2. Close up of the flower.

DETAILED BOTANICAL DESCRIPTION

In the following description, color references are made to The Royal Horticultural Society Colour Chart (2001). Plants used for the description were grown for two years at a nursery in Hebron, Ill., USA. Measurements and numerical values represent averages of typical plants.

Botanical classification: *Sedum* hybrid cultivar Pillow Talk.

Parentage: Male or pollen unknown and female or seed an open pollinated, unnamed *Sedum ussuriense*.

Propagation: Vegetative division and stem cutting propagation.

Plant description: Overall habit of the new *Sedum* is basal clumps, with upright stems topped by red-purple color flowers in September. Growth rate of the new *Sedum* plant is vigorous.

*Plant height*.—Average 45-50 cm.
*Plant width*.—Up to 90 cm.
*Stem color*.—146 C green at the base, 60 A, B and C below the flower.
*Stem shape*.—Both typical and observed — round.
*Stem texture*.—Glabrous.
*Stem length*.—60 cm.
*Stem diameter*.—13 mm.
*Internode length*.—15 mm.

Foliage:
*Type*.—Deciduous.
*Shape*.—Obovate.
*Petiole*.—None.
*Length*.—11 cm.
*Width*.—7 cm.
*Thickness*.—2 mm.
*Margin*.—Dentate.
*Leaf apex, typical and observed*.—Obtuse.
*Leaf bases, typical and observed*.—Cuneate.
*Upper and lower leaf texture*.—Smooth.
*Leaf arrangement*.—Alternate, crowded except at the base of the stems.
*Leaf venation pattern*.—Arcuate.
*Leaf vein color*.—Primary vein color can be 60 A, B and C on the top and the bottom. Color tends to be more prominent with the age of the plant. Secondary vein color is 145 A on top, 147 C on the bottum.
*Adaxial leaf description*.—Color is 139 A.
*Abaxial leaf description*.—Color is 137 C.
*Fall foliage color*.—None noticed.

Flower:
*Petal count*.—5.
*Petal shape*.—Lanceolate.
*Adaxial petal color*.—64 B.
*Abaxial petal color*.—64 B.
*Petal apex shape*.—Acuminate.
*Petal base*.—2 mm wide.
*Petal length*.—5-6 mm.
*Petal width*.—2 mm.
*Petal margin, typical and observed*.—Entire.
*Petal bases, typical and observed*.—Obtuse.
*Inflorescence type*.—Panicle on basal flowering stems.
*Panicle color*.—As a whole the color is close to 71 A.
*Inflorescence size*.—15 cm across, 15 cm tall.
*Inflorescence length*.—15 cm.
*Inflorescence width*.—15 cm.
*Flower number*.—Approximately 750 per panicle.
*Individual flower size*.—10-12 mm across, 4-5 mm tall.
*Bloom period and duration*.—Early September to end of September, lasting three to four weeks.
*Bud shape, typical and observed*.—Elliptical.
*Bud length, typical and observed*.—4-5 mm.
*Bud diameter, typical and observed*.—3 mm.
*Bud color, typical and observed*.—Close to 139 A.
*Sepal size*.—1 mm across, 2 mm tall.
*Sepal number*.—5.
*Sepal shape, typical and observed*.—Narrow ovate.
*Sepal apex, typical and observed*.—Acute.
*Sepal margin, typical and observed*.—Entire.
*Sepal color, abaxial and adaxial typical and observed*.—Close to 138 D.
*Peduncle length, typical and observed*.—25 mm.
*Peduncle diameter, typical and observed*.—1-2 mm.
*Peduncle color, typical and observed at the beginning of the season usually April, May, and June*.—Close to 139 A. As the season progresses usually July, August, September, and October typical and observed peduncle color can be — 60 A, B and C.
*Pedicel length, typical and observed*.—2 mm.
*Pedicel diameter, typical and observed*.—1 mm.
*Pedicel color, typical and observed at the beginning of the season usually April, May, and June*.—Close to 139 A. As the season progresses usually July, August, September, and October typical and observed peduncle color can be — 60 A, B and C.
*Carpel color*.—71 B.
*Carpel surfaces*.—Glabrous.
*Carpel number*.—5 per flower.
*Stigma shape*.—Capitate, Stigma size — 2-3 mm, Stigma color — 71 B.
*Style length*.—1-2 mm, Style shape slender, Style color — 71 B.
*Ovary size*.—1-2 mm, Ovary shape — cordate, Ovary color — 71 B.
*Fertility*.—Sterile, 10 anthers, 10 stamens at 7 mm long, color 72 B.
*Anther color*.—Close to N187 C, Pollen color — 21 B.
*Blooming habit*.—Domed, terminal panicle on up to 60 cm stems.
*Scent*.—No scent noticed.
*Fruit*.—None noticed.
*Hardiness*.—U.S.D.A. hardiness zones 4-9.
*Disease resistance*.—Resistance to *Rhizoctonia* a disease common to *Sedum* has been observed on plants grown under nursery conditions.
*Pest resistance*.—Resistance to pests common to *Sedum* has not been, observed on plants grown under nursery conditions.

I claim:

1. A new, distinct *Sedum* plant as illustrated and described, characterized by larger green foliage, red-purple color flowers, and taller height, compared to the seed parent.

* * * * *